United States Patent [19]

Bastioli et al.

[11] Patent Number: 5,534,150
[45] Date of Patent: Jul. 9, 1996

[54] SELECTIVELY-PERMEABLE MEMBRANE AND THE USE THEREOF

[75] Inventors: Catia Bastioli, Novara; Vittorio Bellotti, Fontaneto D'Agogna, both of Italy

[73] Assignee: Novamont S.P.A., Milan, Italy

[21] Appl. No.: 245,065

[22] Filed: May 17, 1994

Related U.S. Application Data

[63] Continuation of Ser. No. 875,453, Apr. 29, 1992, abandoned.

[30] Foreign Application Priority Data

May 3, 1991 [IT] Italy .................................. TO91A0327

[51] Int. Cl.⁶ .................................................. B01D 61/36
[52] U.S. Cl. ................ 210/640; 210/500.28; 210/500.42
[58] Field of Search .............................. 210/640, 500.28, 210/500.42, 500.35, 500.34; 427/2

[56] References Cited

U.S. PATENT DOCUMENTS

| | | |
|---|---|---|
| 3,652,542 | 3/1972 | Hjermstad . |
| 4,673,328 | 6/1987 | Wittwer et al. . |
| 4,780,411 | 10/1988 | Piejko et al. ............................... 422/56 |
| 4,780,412 | 10/1988 | Piejko et al. . |
| 4,863,655 | 9/1989 | Locourse et al. . |
| 4,900,361 | 2/1990 | Sachetto et al. . |
| 4,985,147 | 1/1991 | Mochizuki et al. ................ 210/640 X |
| 5,035,930 | 7/1991 | Lacourse et al. . |
| 5,043,196 | 8/1991 | Lacourse et al. . |
| 5,095,054 | 3/1992 | Lay et al. . |

FOREIGN PATENT DOCUMENTS

| | | |
|---|---|---|
| 0032302 | 7/1981 | European Pat. Off. . |
| 0132299 | 1/1985 | European Pat. Off. . |
| 0282451 | 9/1988 | European Pat. Off. . |
| 0298920 | 1/1989 | European Pat. Off. . |
| 0304401 | 2/1989 | European Pat. Off. . |
| 0326517 | 8/1989 | European Pat. Off. . |
| 0327505 | 8/1989 | European Pat. Off. . |
| 0388924 | 9/1990 | European Pat. Off. . |
| 0391853 | 10/1990 | European Pat. Off. . |
| 0404727 | 12/1990 | European Pat. Off. . |
| 0404728 | 12/1990 | European Pat. Off. . |
| 0400532 | 12/1990 | European Pat. Off. . |
| 0404723 | 12/1990 | European Pat. Off. . |
| 0409789 | 1/1991 | European Pat. Off. . |
| 0409788 | 1/1991 | European Pat. Off. . |
| 0409783 | 1/1991 | European Pat. Off. . |
| 0407350 | 1/1991 | European Pat. Off. . |
| 0408501 | 1/1991 | European Pat. Off. . |
| 0408502 | 1/1991 | European Pat. Off. . |
| 0408503 | 1/1991 | European Pat. Off. . |
| 0409781 | 1/1991 | European Pat. Off. . |
| 0409782 | 1/1991 | European Pat. Off. . |
| 8802313 | 2/1988 | United Kingdom . |
| 2190093 | 8/1990 | United Kingdom . |
| WO90/10671 | 9/1990 | WIPO . |
| WO91/02025 | 2/1991 | WIPO . |
| WO91/02024 | 2/1991 | WIPO . |
| WO91/02023 | 2/1991 | WIPO . |

OTHER PUBLICATIONS

*Chemical Abstracts*, vol. 7, No. 8, p. 47, abstract No. 60151n, F. H. Otey et al., "Starch–based blow films" (Aug. 24, 1987).

Otey, F. H. et al., Ind. Eng. Chem. Res. 26(8): 1659–63 (1987), "Starch–Based Blown Films" European Search Report dated Aug. 6, 1992 in European Patent Application EP 92107183 with one-page annex.

Communication dated Aug. 14, 1992.

Patent Abstract of Japan vol. 11, No. 101.

Patent Abstract of Japan vol. 8, No. 19.

*Primary Examiner*—Frank Spear
*Attorney, Agent, or Firm*—Bryan Cave

[57] ABSTRACT

A selectively-permeable membrane constituted by a composition comprising starch and a synthetic thermoplastic polymer is used for separating liquid aqueous-organic mixtures by pervaporation.

25 Claims, No Drawings

SELECTIVELY-PERMEABLE MEMBRANE AND THE USE THEREOF

This is a continuation of U.S. application Ser. No. 07/875,453, filed Apr. 29, 1992, now abandoned.

DESCRIPTION

The present invention relates to methods of separating liquid mixtures with selectively-permeable membranes and, in particular, to pervaporation methods.

Pervaporation is a method of separation by means of a membrane, and is used industrially for fractionating mixtures of liquids which, from the point of view of energy usage, cannot be treated economically by conventional distillation methods and, in particular, for separating the components of an azeotropic mixture or a mixture of components having almost equal volatility.

The method consists of the circulation of the mixture in contact with a thin, non-porous, selectively-permeable membrane, the opposite face of which is kept under low pressure, the vapours which pass though the membrane being removed by pumping or by a continuous flow of inert gas. The permeate may be condensed on a cold surface for collection or recycling.

Pervaporation methods are currently used industrially, particularly for dehydrating binary mixtures of water with ethanol, butanol, tetrahydrofuran, acetone, methyl ethyl ketone, chloroform and ethyl acetate.

The selection of the material constituting the membrane determines the separation characteristics. Thus it is known that aqueous-organic mixtures can be dehydrated with the use of hydrophilic membranes about 20 microns thick formed by polyvinyl alcohol, polyacrylic acid, or polyuronides (such as alginates and chitosan). Hydrophobic membranes of polymers such as silicones, some cellulose ethers, polyacetylene and polyperfluoroacrylate polymers may be used to separate volatile species contaminating an aqueous medium.

The present invention is based on the discovery that polymeric starchy compositions including synthetic thermoplastic polymers have properties of selective permeability and can thus be used to produce membranes useful in methods of separating liquid aqueous-organic mixtures by pervaporation, particularly in order to dehydrate them.

A subject of the present invention is therefore a method of separating liquid aqueous-organic mixtures with the use of a selectively-permeable membrane, characterised in that the membrane is constituted by a composition comprising starch and at least one synthetic thermoplastic polymer. Starchy polymeric compositions including synthetic thermoplastic polymers known from the literature, for example, such as those described in patent applications EP-A-327505, EP-A-404723, EP-A-408503, EP-A-413798 and EP-A-400532, may be used within the scope of the present invention.

Such compositions are obtainable by blending the starch-based component and the synthetic polymer component, under extrusion cooking conditions in the presence of water and/or of a plasticizer (typically 5–40% wt of water or plasticizer referred to the starch/water system) at a temperature sufficient to form a thermoplastic melt.

Of the polymers described in these documents, the use of polymers which are substantially insoluble in water but not substantially hydrophobic is preferable, the term "not substantially hydrophobic" meaning polymers and copolymers with water absorption of more than 2% and, preferably, more than 4% but less than 30% by weight under equilibrium conditions at ambient temperature (20° C.).

However, essentially hydrophobic polymers may also be used, provided that they are mixed in small quantities with polymers which are not substantially hydrophobic.

The concentration of the synthetic polymer compared with the quantity of anhydrous starch may vary from 5 to 60% by weight referred to the sum of the anhydrous starch and synthetic polymer components, but in any case must be such that the permeability of the membrane by the liquid to be evaporated is the maximum which is consistent with a high degree of selectivity.

Moreover, exposure to the liquid mixture to be separated should not result in a loss of mechanical properties such as to compromise the functionality of the membrane. This aspect is particularly important for self-supporting membranes of the order of tens of microns thick. In the case of composite membranes with generally hydrophobic porous polymeric substrates, in which the permeable membrane may be of the order of microns thick, the level of mechanical properties required may be lower.

As the synthetic polymeric component, olefinic polymers including repeating units each having at least one polar functional group such as a hydroxyl, alkoxyl, carboxyl, carboxyalkyl, alkylcarboxyl, halogen or acetal groups are contemplated. Of these, polyvinyl alcohol, copolymers of an olefinic monomer selected from ethylene, propylene, isobutene and styrene with acrylic acid, methacrylic acid and salts thereof, vinyl alcohol and vinyl acetate are considered in particular. Polymers of polyvinylpyrrolidone/vinyl acetate, polyvinylpyridine and polyhydroxyethyl methacrylate may also be used. Particularly preferred are polyvinyl alcohols and ethylene-vinyl alcohol copolymers containing less than 40% by weight of ethylene with various degrees of hydrolysis produced, respectively, by hydrolysis of the corresponding polyvinyl acetate and ethylene-vinyl acetate. The ethylene-vinyl alcohol copolymer preferably has a degree of hydrolysis of between 50 and 100%.

The alcohol groups of the polymers mentioned above may be partially or completely modified to produce:

1) ethers resulting from reaction with:
   ethylene oxide
   ethylene oxide substituted with alkyl radicals up to $C_{20}$ or with aromatic radicals
   acrylonitrile ($Ce^{2+}$ initiator)
   acrylamide
   arylalkylhalides
   chloroacetic acid
   methylchloromethyl ether
   silanes 2) inorganic and organic esters such as sulphates, nitrates, phosphates, arsenates, xanthates, carbamates, urethanes, borates, titanates, 3) organic esters resulting from reaction with aliphatic or aromatic acids, chloroacyls, particularly of fatty acids, anhydrides, 4) acetals and ketals produced by reaction with
   aliphatic aldehydes with up to 22 carbon atoms,
   unsaturated aliphatic aldehydes with up to 22 carbon atoms,
   chloroacetaldehyde
   glyoxal
   aromatic aldehydes
   cyclic aliphatic aldehydes,
   aliphatic ketones arylalkyl ketones
alkylcycloalkyl ketones.

The reactions which produce the ethers, organic and inorganic esters and the acetals given above can easily be brought about as described in Chapter 9 and in the literature cited in the publication "Polyvinyl alcohol" edited by C. A. Finch.

It is also possible to use multifunctional polymers of polyvinyl alcohol and of ethylene-vinyl alcohol (containing up to 40% by weight of ethylene with degrees of hydrolysis of the acetate of between 100 and 50%), in which up to 50% of the ethylene may be substituted by co-monomers selected from the group consisting of:

propylene, isobutene, styrene, vinyl chloride, 1,1-dichloroethene, vinyl ethers of the formula $CH_2=CR-OR'$ in which R is hydrogen or a methyl group and R' is an alkyl group with from 1 to 18 carbon atoms, a cycloalkyl group or a polyether, acrylonitrile, methacrylonitrile, vinyl ketones of the formula $CH_2=CR-CO-CH_2-R'$ in which R is hydrogen or a methyl group and R' is hydrogen or a $C_1-C_6$ alkyl group, acrylic or methacrylic acid and their esters of the formula $CH_2=CR-COOR'$ in which R is hydrogen or a methyl group and R' is hydrogen or a $C_1-C_6$ alkyl group, and the alkali metal or alkaline-earth metal salts of those acids, vinyl derivatives of the formula $CH_2=CR-OCOR'$ in which R is hydrogen or a methyl group and R' is hydrogen, a methyl group, a methyl group mono-, bi-, or tri-substituted with chloro- or fluoro- groups, or a $C_2-C_6$ alkyl group, vinyl carbamates of the formula $CH_2=CR-CONR'R''$ in which R is hydrogen or a methyl group and R' and R'' are the same or different and are hydrogen or $C_1-C_3$ alkyl groups, maleic anhydride, fumaric anhydride, vinylpyrrolidone, vinylpyridine, or 1-vinylimidazole.

The copolymerisation is achieved with the use of radical initiators such as hydrogen peroxide, peroxysulphates and benzoyl peroxides, as described in the chapter "Polymerisation processes of vinyl esters" and the literature cited on pages 406 et. seq. of Volume 17 of the "Encyclopedia of Polymer Science and Engineering"

It is also possible to use compositions including starch, ethylene-vinyl alcohol copolymer, possibly modified, and hydrophobic polymers of polyethylene or of its vinyl copolymers such as those mentioned above, or aliphatic polyesters (e.g. polyvinyl acetate, poly-epsilon caprolactone, polyhydroxybutyrate (PHB) and polyhydroxybutyrate valerate (PHBV), polylactic acid, polyethylene and polybutylene adipates or sebacates), polyethers (e.g. polyoxymethylene, polyoxyethylene, polyoxypropylene, polyphenylene oxide), polyamides (nylon 6, nylon 12, etc.), polyacrylonitrile, polyurethanes, polyester/polyurethane copolymers, polyester/polyamide copolymers, polyglycolide, hydrophilic polymers such as polyvinylpyrrolidone, polyoxazoline, cellulose acetates and nitrates, regenerated cellulose, alkyl cellulose, carboxymethyl cellulose, casein-type proteins and salts thereof, natural gums such as gum arabic, algin and alginates, chitin and chitosan.

The starch used in the polymeric compositions is preferably a native starch extracted from vegetables such as potatoes, rice, tapioca, maize and cereals. In any case, the term starch is intended also to include physically and chemically modified starches, provided that the product of the interpenetration of the starch and the synthetic polymer is insoluble in water.

The polymeric composition constituting the membrane preferably includes a plasticiser at a concentration of from 1 to 50% by weight, preferably from 5 to 40% with reference to the weight of the total composition. Polyols selected from the following may be used as the plasticiser:

a) polyols formed by from 1 to 20 repeating hydroxylated units each including from 2 to 6 carbon atoms, b) ethers, thioethers, inorganic and organic esters, acetals and amino-derivatives of polyols formed by from 1 to 20 repeating hydroxylated units each including from 2 to 6 carbon atoms, c) reaction products of polyols having from 1 to 20 repeating hydroxylated units each including from 2 to 6 carbon atoms with chain extenders, d) oxidation products of polyols having from 1 to 20 repeating hydroxylated units each including from 2 to 6 carbon atoms including at least one aldehydic or carboxylic functional group or a mixture thereof.

Compounds which have vapour pressures below that of glycerine at ambient temperature (25° C.) and which are soluble in water are preferred.

The aliphatic polyols of type a) include compounds of the formula:

$$OH-CH_2-(CHOH)_n-CH_2OH \qquad (I)$$

in which n is from 0 to 4, such as ethylene glycol, glycerol, erythritol, arabitol, adonitol, xylitol, mannitol, iditol, galactitol, sorbitol and allitol and polyols which do not fall within the formula given above, such as propylene glycol, polyglycols, trimethylolpropane, pentaerythritol, polyvinyl alcohol with from 3 to 20 repeating units, and polyglycerol formed by from 2 to 10, preferably from 2 to 5, monomeric units, including mixtures of various oligomers.

The aliphatic polyol derivatives of paragraph b) preferably have structural formulae which can be obtained by the -substitution of at least one alcoholic functional group of the polyol in question, which is preferably selected from those cited in the preceding paragraph, by a functional group selected from:

—O—$(CH_2)_n$—H in which n=1–18, preferably 1–4,

—O—CH=CH—$R_1$ in which $R_1$=H or —$CH_3$,

—$(CH_2-CHR_1-O)_n$—H in which $R_1$=H or $CH_3$ and n=1–20,

—O—$(CH_2)_n$—Ar in which Ar is a sample, substituted, or heterocyclic aromatic radical and n=0–4,

—OCO—H,

—OCO—$CR_1R_2R_3$ in which the $R_1$, $R_2$, and $R_3$ groups are the same or different and are selected from H, Cl, and F, —OCO—$(CH_2)_n$—H in which n=2–18, preferably 2–5,

—$ONO_2$,

—$OPO_3M_2$ in which M may be H, ammonium, an alkali metal, an alkaline earth, or an organic cation, particularly trimethylammonium, pyridinium or picoline, —$SO_3$—AR in which Ar is benzene or toluene, —OCO—$CH(SO_3M)$—COOM in which the Ms are the same or different and are selected from H, an alkali metal, an alkaline-earth metal, ammonium, and an organic cation, particularly pyridinium, picoline or methylammonium, —OCO—B—COOM in which B is $(CH_2)_n$ in which n=1–6 or —CH=CH—, M may be H, an alkali metal, an alkaline-earth metal, or —$(CH_2)_n$H in which n=1–6 or an aryl group, —OCONH—$R_1$ in which $R_1$ may be —H or an aliphatic or aromatic radical, —O—(CH$_2$)$_n$—COOM in which n=1–6 and M may be H, an alkali metal, an alkaline-earth metal, ammonium, or an organic cation, particularly pyridinium, trimethylammonium, or picoline, —O—(CH$_2$)$_n$—COOR$_1$ in which n=1–6, R$_1$=H(CH$_2$)$_m$— in which m=1–6, —NR$_1$R$_2$ in which R$_1$ and R$_2$=H, CH$_3$—, CH$_3$CH$_2$—, —CH$_2$—CH$_2$OH or a salified amino group, —O—(CH$_2$)$_n$—NR$_1$R$_2$ in which n=1–4, R$_1$ and R$_2$=H, CH$_3$—, CH$_3$CH$_2$—, or CH$_2$—CH$_2$OH, and in which the amino group may be salified,

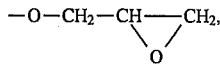

—O—CH$_2$—CHOH—CH$_2$—NR$_1$R$_2$ in which R$_1$ and R$_2$ are the same or different and are selected from H, and H(CH$_2$)$_n$ in which n=1–6 and in which the amino group may be salified, —O—CH$_2$—CHOH—CH$_2$—R$^+_1$Cl$^-$ in which R$^+_1$ is a trialkylammonium, pyridinium or picoline group, —O—(CH$_2$)$_n$R$^+_1$Cl$^-$ in which n=1–6 and R$^+_1$ is a trialkylammonium, pyridinium or picoline group, —O—(CH$_2$)$_n$—CN in which n=1–6, —O—(CH$_2$)$_n$—CONH$_2$ in which n=1–6, —O—(CH$_2$)$_m$—SO$_2$—(CH$_2$)$_n$—H in which m and n=1–4, —SCSNH$_2$, —O—SiX$_3$ and —O—SiOX$_3$ in which X may be an aliphatic or an aromatic radical.

Mono- and di-ethers and mono- and di-esters of the polyols of formula (I) given above are particularly preferred and monoethoxylate, monopropoxylate, and monoacetate derivatives, particularly of sorbitol, are most preferred.

The compounds of paragraph c) result from the joining of two or more polyol molecules by means of chain extenders, in particular such as bicarboxylic acids, aldehydes and isocyanates. Preferred compounds are of the formula:

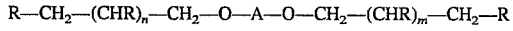

in which n and m are the same or different and have values of from 1 to 6, the R groups are the same or different and are hydroxyl groups or have the meaning given above, and in which A is selected from the group consisting of:

—CHR$_1$ in which R$_1$=H or H—(CH$_2$)$_n$—, in which n=1–5 (acetals),

—(CH$_2$)$_n$— in which n=1–6,

—(CH$_2$—O—CH$_2$)$_n$ in which n=1–20,

—(CH$_2$CH$_2$—O)$_n$—CH$_2$CH$_2$— in which n=1–20,

—OC—(CH$_2$)$_n$—CO — in which n=0–6,

—OC—Ar—CO—in which Ar is an aromatic radical which is also heterocyclic,

—PO$_2$—,

—CONH—(CH$_2$)$_n$NHCO—, and compounds of the formula:

in which n and m are the same or different and are whole numbers from 1 to 6, the R groups are the same or different and are hydroxyl groups or have the meaning given above, and in which A is selected from the group consisting of NH— and —NH—(CH$_2$—CH$_2$—NH)$_n$— in which n is a whole number from 1 to 6.

Of the compounds given above, compounds in which only one of the R groups is a group forming an ether or an ester are preferred.

The term "polyol" is intended to include mono- and polysaccharides having up to 20 monosaccharide units.

The following monosaccharides are considered in particular:

pentoses and their derivatives of the formula:

in which the R groups are the same or different and are hydroxyl groups or have the meaning given above.

Examples of these compounds are arabinose, lyxose, ribose and xylose and, preferably, their monoethers and monoesters, aldohexoses and their derivatives of the formula:

and ketohexoses and their derivatives of the formula:

in which the R groups are the same or different and are hydroxyl groups or have the meaning given above.

Examples of these monosaccharides are glucose, fructose, mannose, allose, altrose, galactose, gulose, idose, inositol, sorbose and talitol.

Of their etherified or esterified derivatives, monoethoxylate - and monopropoxylate derivatives and monoesters, particularly of acetic acid, are preferred.

The polysaccharides include compounds having up to 20 repeating units of formula (II), (III) or (IV) with molecular weights up to that of dextrin.

The R functional groups may be introduced into the basic structure of the polyol by known reactions, for example, as described in Chapter 9 and in the literature cited in the publication "Polyvinyl alcohol" edited by C. A. Finch.

The polymeric material may also include agents, such as urea or hydroxides of alkali metals or of alkaline-earth metals, which can destroy hydrogen bonds and of which quantities of between 0.5 and 20% with reference to the weight of the entire composition are added to the mixture of starch and copolymer.

The polymeric material may also include cross-linking agents such as aldehydes, ketones and glyoxals, process coadjuvants and release agents, and lubricants which are normally incorporated in compositions for moulding or extrusion, such as fatty acids, esters of fatty acids, higher alcohols, polythene waxes, fungicides, flame-proofing agents, herbicides, antioxidants, fertilisers, opacifiers and stabilisers.

The polymeric composition is preferably prepared by the mixing of the components cited above in an extruder heated to a temperature generally between 100 and 220° C. by the methods described in patent applications EP-A-413798 and EP-A-400532 which are incorporated in the present application by references. The composition supplied to the extruder includes water due to the intrinsic water content of the starch used (9–15% by weight) and water may be added as appropriate.

In order, as a result of the moulding or extrusion of the polymeric composition, to obtain sheets useful for producing membranes having suitable mechanical properties, it is preferable to reduce the water content of the total composition during the extrusion by intermediate de-gassing to various contents of between 1.5 and 5% by weight according to the transformation technology and the degree of stiffness required in the final material.

The pressures to which the mixture is subjected during the heat treatment are typical for extrusion in single or double-screw extruders. Although the process is preferably carried out in an extruder, the starch, synthetic polymer and plasticiser may be mixed by any device which ensures conditions of temperature and shearing stress suitable to make the starch and the polymer used compatible from a theological point of view.

If synthetic polymers with high melting points such as, for example, polyvinyl alcohol and ethylene-vinyl alcohol copolymer with an ethylene content no greater than 40% by weight are used in particular, the plasticisers described also perform an important function in the process which leads to the formation of a composition with an (at least partially) interpenetrated structure. The melting points of these polymers (160°–200° C.) are so high that complete interpenetration with the starch molecules is not possible; the addition of plasticisers common to the starchy and polymeric components lowers the melting points of the synthetic polymers and, at the same time, changes their theological behaviour.

The method of the invention for preparing compositions for selectively-permeable membranes under the preferred conditions includes the following steps:

swelling the starch and the synthetic polymer by means of the plasticiser, and possibly water, at a temperature of between 80 and 180° C. with a dynamic change in their melting points and theological behaviour; this effect can be achieved, for example, during a first stage of the transportation of the components through an extruder, for periods of the order of from 2 to 50 seconds, subjecting the mixture to shearing conditions corresponding to similar viscosity values of the two components so as to cause the interpenetration of the molecules of the two components, de-gassing freely or in a controlled manner under pressure or under vacuum to produce a melt at a temperature of 140°–180° C. with a liquid content such that bubbles are not created at atmospheric pressure, that is, for example, at the output of the extruder, cooling the finished product in a water bath or in air.

The entire method requires a pressure of between 0.5 and 10 MPa, preferably between 1 and 5 MPa.

As stated above, the thermoplastic composition is preferably prepared by mixing the components mentioned directly, but the starch may also be treated beforehand in the presence of plasticisers, and possibly added water, with temperature conditions of from 100 to 220° C to produce a thermoplastic starch. This starch may be mixed with the synthetic polymer and a further quantity of plasticiser during a second step. For polyvinyl alcohol and ethylene-vinyl alcohol copolymer, a portion of the total quantity of plasticiser is added at the start of the mixing of the pretreated starch and the synthetic polymer since the plasticiser has to be available to modify the melting point and rheological behaviour of the polymer to make it compatible with the starch.

During the industrial process for separating aqueous-organic mixtures with the use of the selectively-permeable membranes described above, it is preferable to carry out a preliminary step in which the membrane is conditioned by being kept immersed in water or in a liquid medium corresponding to that to be subjected to pervaporation for a period long enough to remove any components which are soluble or susceptible to migration, such as plasticisers which are included in the starch/synthetic polymer matrix, until an equilibrium condition is reached. This step prevents any contamination of the liquid medium during the pervaporation process and does not adversely affect the selective permeability of the membrane. The membranes used preferably have wall thicknesses of from 0.1 to 300 microns, preferably between 0.5 and 30 microns.

Aqueous-organic mixtures which may be separated or of which the organic component may be enriched as a result of the selective permeation of the water include mixtures of water with alcohols with from 1 to 6 carbon atoms, particularly ethanol and butanol, diols, particularly such as ethylene and propylene glycol, triols such as glycerol, -ethers such as diethyl ether, di-isopropyl ether, methyl tert-butyl ether and ketones, particularly such as acetone and methyl ethyl ketone.

EXAMPLE 1

Preparation of the polymeric composition.

| Composition (% wt) | |
|---|---|
| Globe starch 3401 (11% wt H$_2$O) | 41.1% |
| EVOH, having an ethylene content of 42% in moles, hydrolysis degree of the acetate groups 99.5% | 41.1% |
| EAA copolymer with 20% of acrylic acid and a melt index of 2 at 125° C. and 0.325 Kg load | 3.2% |
| Armid E | 0.3% |
| Glycerine | 11.8% |
| Water | 2.5% |

The composition given above was mixed intimately by means of a double-screw OMC extruder with a diameter of 60 mm and an L/D of 36. The operative conditions were as follows:

| ZONE | 1 | 2 | 3 | 4 | 5 | 6 | 7 | 8 | 9 | 10 |
|---|---|---|---|---|---|---|---|---|---|---|
| Temp. °C. | 20 | 90 | 140 | 175 | 175 | 175 | 175 | 175 | 160 | 150 |

Head pressure: 35 bars.

De-gassing was carried out during the operation in order to reduce the water content of the extruded material to 2.5%.

EXAMPLE 2

The granular material produced as described in Example 1 was used to mould bottles with capacities of 150 ml and 625 microns thick.

For this purpose, an AEMME Blow Moulding Machine "AEMME-200" was used, operating under the following temperature conditions:

|  | Zone 1 | Zone 2 | Zone 3 |
|---|---|---|---|
| Cylinder °C. | 145 | 150 | 150 |
| Head °C. | 155 | 155 | — |

The supply screw rotated at 42 rpm; the blowing time was 7 seconds.

EXAMPLE 3

Bottles produced according to Example 2 were filled with absolute ethyl alcohol and weighed accurately. The bottles were placed in an atmosphere with controlled temperature and humidity (20° C. and 50% RH) and the weight loss during the period was recorded.

After 39 days the weight loss was 3.30%.

EXAMPLE 4

Bottles produced according to Example 2 were filled with water:ethyl alcohol mixed at a ratio of 92:8 by volume, which corresponds to an initial alcohol content of 6.4% by weight, measured by gas chromatography. The bottles were placed in a controlled environment (20° C. and 50% RH).

After 27 days, the average alcohol concentration was 12.1% by weight and the overall weight loss was 56.6%.

EXAMPLE 5

Further bottles were filled with a 1:1 water:ethyl alcohol mixture by volume, which is equal to an alcohol concentration of 44.1% by weight measured by GC.

After 42 days, the average alcohol concentration had risen to a value of 82.0% by weight, whereas the overall weight loss remained at 61.6%.

EXAMPLE 6

Further bottles were filled with a 4:96 water:ethyl alcohol mixture by volume, which is equal to a concentration of 94.75% by weight measured by GC.

This composition is similar to the azeotropic composition of an ethanol-water system.

The bottles were placed under a glass bell jar and kept in a flow of dry nitrogen. The test temperature was 20° C.

After 11 days, the ethyl alcohol concentration had risen to 97.2% by weight whilst an overall loss of weight of 3.2% was recorded.

EXAMPLE 7

Further bottles according to Example 2 were filled with a commercial dry white wine with 11 degrees of alcohol, corresponding to a concentration of 8.4% by weight measured by GC.

After 26 days in an environment with controlled temperature and humidity (20° C. and 50% RH) the alcohol concentration of the wine had risen to 14.9% by weight with an overall weight loss of 41.8%.

EXAMPLES 8–10

The procedure of example 1 was repeated by modifying the composition according to the following:

|  |  | Ex 8 | Ex 9 | Ex 10 |
|---|---|---|---|---|
| Globe starch 3401 (11% H$_2$O) | % wt | 62.2 | 52.2 | 62.2 |
| EVOH (example 1) | % wt | 20 | 30 | 23.2 |
| EAA (example 1) | % wt | 3.2 | 3.2 | — |

The % amount of the other components cited in example 1 was not changed.

Bottles obtained from the compositions of examples 8, 9 and 10, according to the procedure of example 2 were used in pervaporation tests according to each of examples 3 to 7 and in all cases an increase of the alcoholic concentration was determined.

We claim:

1. A method of separating liquid aqueous-organic mixtures by pervaporation with the use of a selectively-permeable membrane, wherein the membrane is constituted by a composition comprising non-ionic starch and at least one synthetic thermoplastic polymer, wherein the non-ionic starch and the synthetic polymer are at least partially interpenetrated to provide a substantially water-insoluble material.

2. A method according to claim 1, wherein the synthetic polymer of the selectively-permeable membrane is an olefinic polymer including repeating units each having at least one polar functional group.

3. A method according to claim 2, wherein the olefinic polymer is selected from the group consisting of polyvinyl alcohol, copolymers of an olefinic monomer selected from ethylene, propylene, isobutene and styrene with a monomer selected from acrylic acid, methacrylic acid and salts thereof, vinyl alcohol and vinyl acetate and mixtures thereof.

4. A method according to claim 2, wherein the olefinic polymer is selected from the group consisting of polyvinylpyrrolidone/vinyl acetate, polyvinylpyridine and polyhydroxyethyl methacrylate.

5. A method according to claim 2 wherein the olefinic polymer is a polymer of ethylene-vinyl alcohol produced by the hydrolysis of the corresponding ethylene-vinyl acetate with a degree of hydrolysis of the acetate groups of from 50 to 100% and an ethylene content of less than 40% by weight.

6. A method according to claim 2, wherein the olefinic polymer is a polymer of ethylene-vinyl alcohol or polyvinyl alcohol having alcoholic functional groups which are at least partially etherified by reaction with a compound selected from the group consisting of ethylene oxide unsubstituted or substituted with $C_1$–$C_{20}$ alkyl radicals or with aromatic radicals, acrylonitrile, acrylamide, arylalkylhalides, chloroacetic acid, methylchloromethyl ether and silanes.

7. A method according to claim 2, wherein the olefinic polymer is a polymer of ethylene-vinyl alcohol or polyvinyl alcohol including esterified alcoholic functional groups selected from the group consisting of sulfates, nitrates, phosphates, arsenates, xanthates, borates, titanates, urethanes and carbomates.

8. A method according to claim 2, wherein the olefinic polymer is a polymer of ethylene-vinyl alcohol or polyvinyl alcohol including alcoholic functional groups which have been esterified by reaction with aliphatic or aromatic acids, chloroacyls or anhydrides.

9. A method according to claim 2, wherein the olefinic polymer is a polymer of ethylene-vinyl alcohol or polyvinyl alcohol including acetal functional groups produced by reaction with compounds selected from the group consisting of saturated and unsaturated aliphatic aldehydes having up to 22 carbon atoms, aromatic aldehydes, cycloaliphatic aldehydes, chloroacetaldehyde, glyoxal, aliphatic ketones, alkylcycloalkyl ketones and arylalkyl ketones.

10. A method according to claim 2, wherein the olefinic polymer is a multifunctional ethylene-vinyl alcohol copolymer with an ethylene content of up to 40% by weight and with a degree of hydrolysis of the acetate of between 100 and 50%, in which up to 50% of the ethylene may be substituted by co-monomers selected from the group consisting of: propylene, isobutene, styrene, vinyl chloride, 1,1-dichloroethene, vinyl ethers of the formula $CH_2=CR-OR'$ in which R is hydrogen or a methyl group and R' is an alkyl group with from 1 to 18 carbon atoms, a cycloalkyl group or a polyether, acrylonitrile, methacrylonitrile, vinyl ketones of the formula $CH_2=CR-CO-CH_2-R'$ in which R is hydrogen or a methyl group and R' is hydrogen or a $C_1-C_6$ alkyl group, acrylic acid, methacrylic acid and their esters of the formula $CH_2=CR-COOR'$ in which R is hydrogen or a methyl group and R' is hydrogen or a $C_1-C_6$ alkyl group, and the alkali metal or alkaline-earth metal salts of those acids, vinyl derivatives of the formula $CH_2=CR-OCOR'$ in which R is hydrogen or a methyl group and R' is hydrogen, a methyl group, a methyl group mono-, bi-, or trisubstituted with chloro- and fluoro- groups, or a $C_2-C_6$ alkyl group, vinyl carbamates of the formula $CH_2=CR-CONR'R''$ in which R is hydrogen or a methyl group and R' and R'' are the same or different and are hydrogen or $C_1-C_3$ alkyl groups, maleic anhydride, fumaric anhydride, vinylpyrrolidone, vinylpyridine, or 1-vinylimidazole.

11. A method according to claim 1, wherein the membrane composition comprises non-ionic starch, at least an olefinic polymer selected from the group consisting of ethylene-vinyl alcohol and polyvinyl alcohol copolymer, and a polymer selected from hydrophobic polymers of polyethylene or of its vinyl copolymers, aliphatic polyesters including polyvinyl acetate, polyepsilon caprolactone, polyhydroxybutyrate, polyhydroxybutyrate valerate, polylactic acid, polyethylene and polybutylene adipates and sebacates, polyethers including polyoxymethylene, polyoxyethylene, polyoxypropylene, and polyphenylene oxide, polyamides, polyacrylonitrile, polyurethanes, polyester/polyurethane copolymers, polyester/polyamide copolymers, polyglycolide, and hydrophilic polymers including polyvinylpyrrolidone, polyoxazoline, cellulose acetates and nitrates, regenerated cellulose, alkyl cellulose, carboxymethyl cellulose, casein-type proteins and salts thereof, natural gums, chitin and chitosan.

12. A method according to claim 1, wherein the membrane composition includes from 5 to 60% by weight of synthetic polymer with reference to the weight of the anhydrous starch.

13. A method according to claim 1, wherein the membrane composition further comprises a plasticiser selected from the group consisting of:

a) polyols formed by from 1 to 20 repeating hydroxylated units each including 2 to 6 carbon atoms;

b) ethers, thioethers, inorganic and organic esters, acetals and amino-derivatives of polyols formed by from 1 to 20 repeating hydroxylated units each including from 2 to 6 carbon atoms;

c) reaction products of polyols having from 1 to 20 repeating hydroxylated units each including from 2 to 6 carbon atoms with chain extenders; and d) oxidation products of polyols having from 1 to 20 repeating hydroxylated units each including from 2 to 6 carbon atoms, and including at least one aldehydric or carboxylic functional group or a mixture thereof.

14. A method according to claim 13, wherein the plasticiser is selected from the group consisting of ethylene glycol, propylene glycol, polyglycols, glycerol, polyglycerols having from 2 to 10 monomeric units, polyvinyl alcohol having from 3 to 20 monomeric units, erthythritol, arabitol, adonitol, xylitol, mannitol, iditol, galactitol, allitol, trimethylolpropane, pentaerythritol, and sorbitol.

15. A method according to claim 13, wherein the plasticiser is a monoethoxylate, monopropoxylate or monoacetate derivate of a polyol, the polyol being selected from the from the group consisting of ethylene glycol, propylene glycol, polyglycols, glycerol, polyglycerols having from 2 to 10 monomeric units, polyvinyl alcohols having from 3 to 20 monomeric units, erthythritol, arabitol, adonitol, xylitol, mannitol, iditol, galactitol, allitol, trimethylolpropane, pentaerythritol, and sorbitol.

16. A method according to claim 13, wherein the plasticiser is a derivative of an aliphatic polyol having from 3 to 6 carbon atoms, in which at least one alcoholic functional group is replaced by a functional group R selected from the group consisting of:

—O—$(CH_2)_n$—H in which n=1–18,

—O—CH=CH—$R_1$ in which $R_1$=H or —$CH_3$,

—O—$(CH_2-CHR_1-O)_n$—H in which $R_1$=H or $CH_3$ and n=1–20,

—O—$(CH_2)_n$—Ar in which Ar is a simple, substituted, or heterocyclic aromatic radical and n=0–4,

—OCO—H,

—OCO—$CR_1R_2R_3$ in which the $R_1$, $R_2$, and $R_3$ groups are the same or different and are selected from H, Cl, and F, —OCO—$(CH_2)_n$—H in which n=2–18,

—$ONO_2$,

—$OPO_3M_2$ in which M may be H, ammonium, an alkali metal, an alkaline-earth metal, or an organic cation including trimethylammonium, pyridinium or picoline, —$SO_3$—Ar in which the Ar is benzene or toluene, —OCO—$CH(SO_3M)$—COOM in which the Ms are the same or different and are selected from H, an alkali metal, an alkaline-earth metal, ammonium, and an organic cation including pyridinium, picoline or methylammonium, —OCO—B—COOM in which B is $(CH_2)_n$ in which n=1–6 or —CH=CH—, M may be H, an alkali metal, an alkaline-earth metal, or—$(CH_2)_n$H in which n=1–6, or —CH=CH—, M may be H, an alkali metal, an alkaline-earth metal, or—$(CH_2)_n$H in which n=1–6, or an aryl group, —OCONH—$R_1$ in which $R_1$ may be —H or an aliphatic or aromatic radical, —O—$(CH_2)_n$—COOM in which n=1–6 and M may be H, an alkali metal, an alkaline-earth metal, ammonium, or an organic cation including pyridinium, trimethylammonium, or picoline, —O—$(CH_2)_n$—$COOR_1$ in which n=1–6, $R_1$=H$(CH_2)_n$— in which m=1–6, —$NR_1R_2$ in which $R_1$ and $R_2$=H, $CH_3$—, $CH_3CH_2$—, —$CH_2$—$CH_2OH$ or a salified amino group, —O—$(CH_2)_n$—$NR_1R_2$ in which n=1–4, $R_1$ and $R_2$=H, $CH_3$—, $CH_3CH_2$—, or $CH_2$—$CH_2$—OH and in which the amino group may be salified

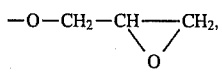

—O—CH$_2$—CHOH—CH$_2$—NR$_1$R$_2$ in which R$_1$ and R$_2$ are the same or different and are selected from H and H(CH$_2$)$_n$ in which n=1–6 and in which the amino group may be salified, —O—CH$_2$—CHOH—CH$_2$R$^+_1$Cl$^-$ in which R$^+_1$ is a trialkylammonium, pyridinium or picoline group, —O—(CH$_2$)$_n$—CN in which n=1–6, —O—(CH$_2$)$_n$—CONH$_2$ in which n=1–6, —O—(CH$_2$)$_m$—SO$_2$—(CH$_2$)$_n$—H in which m and n=1–4,

—SCSNH$_2$,

—O—SiX$_3$ and —O—SiOX$_3$ in which X may be an aliphatic or an aromatic radical.

17. A method according to claim 13 wherein the plasticiser is a compound of the formula:

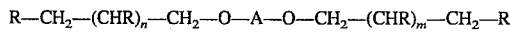

in which n and m are the same or different and have values of from 1 to 6, the R groups are the same or different and are selected from the group consisting of

—OH

—O—(CH$_2$)$_n$—H in which n=1–18,

—O—CH=CH—R$_l$ in which R$_1$=H or —CH$_3$,

—O—(CH$_2$—CHR$_1$—O)$_n$—H in which R$_1$=H or CH$_3$ and n=1–20,

—O—(CH$_2$)$_n$—Ar in which Ar is a simple, substituted, or heterocyclic aromatic radical and n=0–4,

—OCO—H,

—OCO—CR$_1$R$_2$R$_3$ in which the R$_1$, and R$_2$, and R$_3$ groups are the same or different and are selected from H, Cl, and F, —OCO—(CH$_2$)$_n$—H in which n=2–18,

—ONO$_2$,

—OPO$_3$M$_2$ in which M may be H, ammonium, an alkali metal an alkaline-earth metal, or an organic cation including trimethylammonium, pyridinium or picoline, —SO$_3$—Ar in which the Ar is benzene or toluene, —OCO—CH(SO$_3$M)—COOM in which the Ms are the same or different and are selected from H, an alkali metal, an alkaline-earth metal, ammonium, and an organic cation including pyridinium, picoline or methylammonium, —OCO—B—COOM in which B is (CH$_2$)$_n$ in which n=1–6 or —CH=CH—, M may be H, an alkali metal, an alkaline-earth metal, or —(CH$_2$)$_n$H in which n=1–6, or —CH=CH—, M may be H, an alkali metal, an alkaline-earth metal, or —(CH$_2$)$_n$H in which n=1–6, or an aryl group, —OCONH—R$_1$ in which R$_l$ may be —H or an aliphatic or aromatic radical, —O—(CH$_2$)$_n$—COOM in which n=1–6 and M may be H, an alkali metal, an alkaline-earth metal, ammonium, or an organic cation including pyridinium, trimethylammonium, or picoline, —O—(CH$_2$)$_n$—COOR$_1$ in which n=1–6, R$_1$=H(CH$_2$)$_m$— in which m=1–6, —NR$_1$R$_2$ in which R$_1$ and R$_2$=H, CH$_3$—, CH$_3$CH$_2$—, —CH$_2$—CH$_2$OH or a salified amino group, —O—(CH$_2$)$_n$—NR$_1$R$_2$ in which n=1–4, R$_1$ and R$_2$=H, CH$_3$—, CH$_3$CH$_2$—, or CH$_2$—CH$_2$OH and in which the amino group may be salified

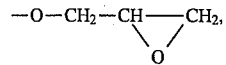

—O—CH$_2$—CHOH—CH$_2$—NR$_1$R$_2$ in which R$_1$ and R$_2$ are the same or different and are selected from H and H(CH$_2$)$_n$ in which n=1–6 and in which the amino group may be salified, —O—CH$_2$—CHOH—CH$_2$—R$^+_1$Cl$^-$ in which R$^+_1$ is a trialkylammonium, pyridinium or picoline group, —O—(CH$_2$)$_n$—CN in which n=1–6, —O—(CH$_2$)$_n$—CONH$_2$ in which n=1–6, —O—(CH$_2$)$_m$—SO$_2$—(CH$_2$)$_n$—H in which m and n=1–4, —SCSNH$_2$, and —O—SiX$_3$ and —O—SiOX$_3$ in which X may be an aliphatic or an aromatic radical;

and in which A is selected from the group consisting of:

—CHR$_1$ in which R$_1$=H or H—(CH$_2$)$_n$— in which n=1–5 (acetals),

—(CH$_2$)$_n$— in which n=1–6,

—(CH$_2$—O—CH$_2$)$_n$ in which n=1–20,

—(CH$_2$CH$_2$—O)$_n$—CH$_2$CH$_2$— in which n=1–20,

—OC—(CH$_2$)$_n$—CO— in which n=0–6,

—OC—Ar—CO— in which Ar is an aromatic radical which is also heterocyclic,

—PO$_2$—, and

—CONH—(CH$_2$)$_n$—NHCO—.

18. A method according to claim 13 wherein the plasticiser is a compound of the formula:

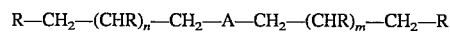

in which n and m are the same or different and are whole numbers from 1 to 6, the R groups are the same or different and are selected from the group consisting of

—OH

—O—(CH$_2$)$_n$—H in which n=1–18,

—O—CH=CH—R$_1$ in which R$_1$=H or —CH$_3$,

—O—(CH$_2$CHR$_1$—O)$_n$—H in which R$_1$=H or CH$_3$ and n=1–20,

—O—(CH$_2$)$_n$—Ar in which Ar is a simple, substituted, or heterocyclic aromatic radical and n=0–4,

—OCO—H,

—OCO—CR$_1$R$_2$R$_3$ in which the R$_1$, R$_2$, and R$_3$ groups are the same or different and are selected from H, Cl, and F, —OCO—(CH$_2$)$_n$—H in which n=2–18,

—ONO$_2$,

—OPO$_3$M$_2$ in which M may be H, ammonium, an alkali metal, an alkaline-earth metal, or an organic cation including trimethylammonium, pyridinium or picoline, —SO$_3$—Ar in which the Ar is benzene or toluene, —OCO—CH(SO$_3$M)—COOM in which the Ms are the same or different and are selected from H, an alkali metal, an alkaline-earth metal, ammonium, and an organic cation including pyridinium, picoline or methylammonium, —OCO—B—COOM in which B is (CH$_2$)$_n$ in which n=1–6 or —CH=CH—, M may be H, an alkali metal, an alkaline-earth metal, or —(CH$_2$)$_n$H in which n=1–6, or —CH=CH—, M may be H, an alkali metal, an alkaline-earth metal, or —(CH$_2$)$_n$H in which n=1–6, or an aryl group, —OCONH—R$_1$ in which R$_1$ may be —H or an aliphatic or aromatic radical, —O—(CH$_2$)$_n$—COOM in which n=1–6 and M may be H, an alkali metal, an alkaline-earth metal, ammonium, or an organic cation including pyridinium, trimethylammonium, or picoline, —O—(CH$_2$)$_n$—COOR$_1$ in which n=1–6, R$_1$=H(CH$_2$)$_m$— in which m=1–6, —NR$_1$R$_2$ in which R$_1$ and R$_2$=H, CH$_3$—, CH$_3$CH$_2$—, —CH$_2$—CH$_2$OH or a salified amino group, —O—(CH$_2$)$_n$—NR$_1$R$_2$ in which n=1–4, R$_1$ and R$_2$=H, CH$_3$—, CH$_3$CH$_2$—, or CH$_2$—CH$_2$OH and in which the amino group may be satisfied

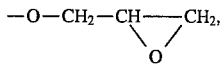

—O—CH$_2$—CHOH—CH$_2$—NR$_1$R$_2$ in which R$_1$ and R$_2$ are the same or different and are selected from H and H(CH$_2$)$_n$ in which n=1–6 and in which the amino group may be salified, —O—CH$_2$—CHOH—CH$_2$—R$^+_1$Cl$^-$ in which R$^+_1$ is a trialkylammonium, pyridinium or picoline group, —O—(CH$_2$)$_n$—CN in which n=1–6, —O—(CH$_2$)$_n$—CONH$_2$ in which n=1–6, —O—(CH$_2$)$_m$—SO$_2$—(CH$_2$)$_n$—H in which m and n=1–4, —SCSNH$_2$, and —O—SiX$_3$ and —O—SiOX$_3$ in which X may be an aliphatic or an aromatic radical;

and in which A is selected from the group consisting of —NH— and —NH—(CH$_2$—CH$_2$—NH)$_n$— in which n is a whole number from 1 to 6.

19. A method according to claim 13 wherein the plasticiser is a compound of the formula:

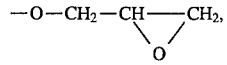 (II)

in which the R groups are the same or different and are selected from the group consisting of

—OH

—O—(CH$_2$)$_n$—H in which n=1–18,

—O—CH=CH—R$_1$ in which R$_1$=H or —CH$_3$,

—O—(CH$_2$—CHR$_1$—O)$_n$—H in which R$_1$=H or CH$_3$ and n=1–20,

—O—(CH$_2$)$_n$—Ar in which Ar is a simple, substituted, or heterocyclic aromatic radical and n=0–4,

—OCO—H,

—OCO—CR$_1$R$_2$R$_3$ in which the R$_1$, R$_2$, and R$_3$ groups are the same or different and are selected from H, Cl and F, —OCO—(CH$_2$)$_n$—H in which n=2–18,

—ONO$_2$,

—OPO$_3$M$_2$ in which M may be H, ammonium, an alkali metal, an alkaline-earth metal, or an organic cation including trimethylammonium, pyridinium or picoline, —SO$_3$—Ar in which the Ar is benzene or toluene, —O—OCO—CH(SO$_3$M)—COOM in which the Ms are the same or different and are selected from H, an alkali metal, an alkaline-earth metal, ammonium, and an organic cation including pyridinium, picoline or methylammonium, —OCO—B—COOM in which B is (CH$_2$)$_n$ in which n=1–6 or —CH=CH—, M may be H, an alkali metal, an alkaline-earth metal, or —(CH$_2$)$_n$H in which n=1–6, or —CH=CH—, M may be H, an alkali metal, an alkaline-earth metal, or —(CH$_2$)$_n$H in which n=1–6, —or an aryl group, —OCONH—R$_1$ in which R$_1$ may be —H or an aliphatic or aromatic radical, —O—(CH$_2$)$_n$—COOM in which n=1–6 and M may be H, an alkali metal, an alkaline-earth metal, ammonium, or an organic cation including pyridinium, trimethylammonium, or picoline, —O—(CH$_2$)$_n$—COOR$_1$ in which n=1–6, R$_1$=H(CH$_2$)$_m$— in which m=1–6, —NR$_1$R$_2$ in which R$_1$ and R$_2$=H, CH$_3$—, CH$_3$CH$_2$—, —CH$_2$—CH$_2$OH or a salified amino group, —O—(CH$_2$)$_n$—NR$_1$R$_2$ in which n=1–4, R$_1$ and R$_2$=H, CH$_3$—, CH$_3$CH$_2$—, or CH$_2$—CH$_2$OH and in which the amino group may be salified

—O—CH$_2$—CHOH—CH$_2$—NR$_1$R$_2$ in which R$_1$ and R$_2$ are the same or different and are selected from H and H(CH$_2$)$_n$ in which n=1–6 and in which the amino group may be salified, —O—CH$_2$—CHOH—CH$_2$—R$^+_1$Cl$^-$ in which R$^+$is a trialkylammonium, pyridinium or picoline group, —O—(CH$_2$)$_n$—CN in which n=1–6, —O—(CH$_2$)$_n$—CONH$_2$ in which n=1–6, —O—(CH$_2$)$_m$—SO$_2$—(CH$_2$)$_n$—H in which m and n=1–4, —SCSNH$_2$, and —O—SiX$_3$ and —O—SiOX$_3$ in which X may be an aliphatic or an aromatic radical.

20. A method according to claim 13, wherein the plasticiser is an aldohexoses or a derivative thereof having the formula:

 (III)

or a ketohexose or a derivative thereof having the formula:

 (IV)

in which the R groups are the same or different and are selected from the group consisting of

—OH

—O—(CH$_2$)$_n$—H in which n=1–18,

—O—CH=CH—R$_1$=in which R$_1$=H or —CH$_3$,

—O—(CH$_2$—CHR$_1$—O)$_n$—H in which R$_1$=H or CH$_3$ and n=1–20,

—O—(CH$_2$)$_n$—Ar in which Ar is a simple, substituted, or heterocyclic aromatic radical and n=0–4,

—O—OCO—H,

—OCO—CR$_1$R$_2$R$_3$ in which the R$_1$, R$_2$, and R$_3$ groups are the same or different and are selected from H, Cl, and F, —OCO—(CH$_2$)$_n$—H in which n=2–18,

—ONO$_2$,

—OPO$_3$M$_2$ in which M may be H, ammonium, an alkali metal, an alkaline-earth metal, or an organic cation including trimethylammonium, pyridinium or picoline, —SO$_3$—Ar in which the Ar is benzene or toluene, —OCO—CH(SO$_3$M)—COOM in which the Ms are the same or different and are selected from H, an alkali metal, an alkaline-earth metal, ammonium, and an organic cation including pyridinium, picoline or methylammonium, —OCO—B—COOM in which B is (CH$_2$)$_n$ in which n=1–6 or —CH═CH—, M may be H, an alkali metal, an alkaline-earth metal, or —(CH$_2$)$_n$H in which n=1–6, or —CH═CH—, M may be H, an alkali metal, an alkaline-earth metal, or —(CH$_2$)$_n$H in which n=1–6, 3or an aryl group, —OCONH—R$_1$ in which R$_1$ may be —H or an aliphatic or aromatic radical, —O—(CH$_2$)$_n$—COOM in which n=1–6 and M may be H, an alkali metal, an alkaline-earth metal, ammonium, or an organic cation including pavridinium, trimethylammonium, or picoline, —O—(CH$_2$)$_n$—COOR$_1$ in which n=1–6, R$_1$=H(CH$_2$)$_m$— in which m=1–6, —NR$_1$R$_2$ in which R$_1$ and R$_2$=H, CH$_3$—, CH$_3$CH$_2$—, —CH$_2$—CH$_2$OH or a salified amino group, —O—(CH$_2$)$_n$—NR$_1$R$_2$ in which n=1–4, R$_1$ and R$_2$=H, CH$_3$—, CH$_3$CH$_2$—, or CH$_2$—CH$_2$OH and in which the amino group may be salified

—O—CH$_2$—CH——CH$_2$,
           \\   /
            O

—O—CH$_2$—CHOH—CH$_2$—NR$_1$R$_2$ in which R$_1$ and R$_2$ are the same or different and are selected from H and H(CH$_2$)$_n$ in which n=1–6 and in which the amino group may be salified, —O—CH$_2$—CHOH—CH$_2$—R$^+_1$Cl$^-$ in which R$^+_1$ is a trialkylammonium, pyridinium or picoline group, —O—(CH$_2$)$_n$—CN in which n=1–6, —O—(CH$_2$)$_n$—CONH$_2$ in which n=1–6, —O—(CH$_2$)$_m$—SO$_2$—(CH$_2$)$_n$—H in which m and n=1–4, —SCSNH$_2$, and —O—SiX$_3$ and —O—SioX$_3$ in which X may be an aliphatic or an aromatic radical.

21. A method according to claim 13, wherein the plasticiser is selected from the group consisting of arabinose, lyxose, ribose, xylose, glucose, fructose, mannose, allose, altrose, galactose, gulose, idose, inositol, sorbose, talitol and their monoethyloxylate, monopropoxylate and monoacetate derivatives.

22. A method according to claim 13, wherein the plasticiser d) is the product of oxidation with an oxidizing reagent selected from periodic acid, hypochlorite and lead tetracetare.

23. A method according to claim 13, wherein the membrane composition contains from 1 to 50% by weight of the plasticiser, with reference to the weight of the composition.

24. A method according to claim 19, wherein all but one of the R groups is an —OH group.

25. A method according to claim 20, wherein all but one of the R groups is an —OH group.

\* \* \* \* \*

UNITED STATES PATENT AND TRADEMARK OFFICE
CERTIFICATE OF CORRECTION

PATENT NO. : 5,534,150

DATED : July 9, 1996

INVENTOR(S) : Catia Bastioli et al.

Page 1 of 2

It is certified that error appears in the above-indentified patent and that said Letters Patent is hereby corrected as shown below:

Column 4 Line 23: Delete "OH-$CH_2$-$(CHOH)_n$n-$CH_2OH$" Insert --OH-$CH_2$-$(CHOH)_n$-$CH_2OH$--

Column 4 Line 35: Delete "-substitution" Insert --substitution--

Column 4 Line 41: Delete "-$(CH_2$-$CHR_1$-$O)_n$-H" Insert ---O$(CH_2$-$CHR_1$-$O)_n$-H--

Column 4 Line 43: Delete "sample" Insert --simple--

Column 7 Line 13: Delete "theological" Insert --rheological--

Column 7 Line 26: Delete "theological" Insert --rheological--

Column 7 Line 33: Delete "theological" Insert --rheological--

Column 13 Line 9: Delete "$CH_2R^+_1Cl^-$" Insert --$CH_2$-$R^+_1Cl^-$--

Column 18 Line 28-29: Delete "tetracetare" Insert --tetracetate--

Column 12 Line 61: Delete "$R_1 = H(CH_2)_n$" Insert --$R_1 = H(CH_2)_m$--

Column 12 Line 66: Delete "$CH_2$-$CH_2$-OH" Insert --$CH_2$-$CH_2OH$--

Column 15 Line 17: Delete "satisfied" Insert --salified--

Column 16 Line 9: Delete "-or" Insert --or--

Column 16 Line 33: Delete "$R^+$is" Insert --$R^+_1$ is--

Column 16 Line 67: Delete "-O-OCO-H," Insert --OCO-H,--

Column 17 Line 21: Delete "3or" Insert --or--

Column 17 Line 26: Delete "pavridinium" Insert --pyridinium--

UNITED STATES PATENT AND TRADEMARK OFFICE
CERTIFICATE OF CORRECTION

PATENT NO. : 5,534,150

DATED : July 9, 1996

INVENTOR(S) : Catia Bastioli et al.

It is certified that error appears in the above-indentified patent and that said Letters Patent is hereby corrected as shown below:

Column 18 Line 16: Delete "SioX$_3$" Insert --SiOX$_3$--

Signed and Sealed this

Twenty-ninth Day of October 1996

Attest:

BRUCE LEHMAN

Attesting Officer

Commissioner of Patents and Trademarks